United States Patent
Kraitzer (10) Patent No.: US 11,304,850 B2
(45) Date of Patent: Apr. 19, 2022

(54) APPARATUS AND METHOD FOR TREATING OR/AND REFRESHING AN EAR CANAL

(71) Applicant: EARWAYS MEDICAL LTD, Rosh HaAyin (IL)

(72) Inventor: Amir Kraitzer, Herzliya (IL)

(73) Assignee: EARWAYS MEDICAL LTD., Rosh Haayin (IL)

( * ) Notice: Subject to any disclaimer, the term of this patent is extended or adjusted under 35 U.S.C. 154(b) by 360 days.

(21) Appl. No.: 16/484,056

(22) PCT Filed: Mar. 23, 2018

(86) PCT No.: PCT/IB2018/051965
§ 371 (c)(1),
(2) Date: Aug. 6, 2019

(87) PCT Pub. No.: WO2018/172981
PCT Pub. Date: Sep. 27, 2018

(65) Prior Publication Data
US 2020/0093644 A1 Mar. 26, 2020

Related U.S. Application Data

(60) Provisional application No. 62/475,920, filed on Mar. 24, 2017.

(51) Int. Cl.
*A61F 11/00* (2006.01)
(52) U.S. Cl.
CPC ..... *A61F 11/006* (2013.01); *A61F 2210/0076* (2013.01); *A61F 2230/0091* (2013.01)
(58) Field of Classification Search
CPC ............... A61F 11/00; A61F 11/006; A61F 2210/0076; A61F 2210/0662;
(Continued)

(56) References Cited

U.S. PATENT DOCUMENTS 3,422,186 A 1/1969 Sasmor
3,923,061 A 12/1975 Rossignol
(Continued)

FOREIGN PATENT DOCUMENTS

CN 2626465 Y 7/2004
CN 2693206 Y 4/2005
(Continued)

OTHER PUBLICATIONS

EarWay TM Pro Tutorial (Earways Medical) Jun. 18, 2017 (Jun. 18, 2017); retrieved from the internet Jun. 22, 2018; <URL=https://www.youtube.com/watch?v=AlmzbJHPLvc>; entire document.
(Continued)

*Primary Examiner* — Robert A Lynch
(74) *Attorney, Agent, or Firm* — The Roy Gross Law Firm, LLC; Roy Gross (57) ABSTRACT

Apparatus and method for treating or/and refreshing an ear canal of a subject, focused on cleaning the ear canal via removing cerumen therefrom. Apparatus includes a treating element formed as an elastic helically shaped coil strip, whose outer and inner surfaces may be coated (covered) by different possible combinations of outer layer, inner layer, and lubrication layer, coatings (coverings). The treating element outer and inner surfaces, as well as the outer layer, inner layer, or/and lubrication layer, are formed of, or/and include, materials exhibiting specific physicochemical properties and characteristics that facilitate particular friction and lubrication phenomena during implementation, which improve efficacy, safety, or/and tolerability of using the apparatus. Also disclosed is a method, including use of the apparatus, for treating or/and refreshing an ear canal of a subject.

20 Claims, 3 Drawing Sheets

(58) Field of Classification Search
CPC ...... A61F 2210/0675; A61F 2230/0091; A61F 13/38; A61M 31/00; A47K 7/00; A47K 7/04; A47K 7/043; A61B 17/221; A61B 17/24; A61B 2017/2215; A61B 2017/2217; A61B 2017/246; A61B 10/02; A61B 10/0275

See application file for complete search history.

(56) References Cited

U.S. PATENT DOCUMENTS

| | | | |
|---|---|---|---|
| 4,895,875 | A | 1/1990 | Winston |
| 5,296,472 | A | 3/1994 | Sanchez et al. |
| 5,380,711 | A | 1/1995 | Sanchez et al. |
| 5,390,663 | A | 2/1995 | Schaefer |
| 5,480,658 | A | 1/1996 | Melman |
| 5,490,859 | A | 2/1996 | Mische et al. |
| 5,820,319 | A | 10/1998 | Hull et al. |
| 5,888,199 | A | 3/1999 | Karell et al. |
| 6,090,079 | A | 7/2000 | Fu |
| 6,152,940 | A | 11/2000 | Carter |
| 6,155,987 | A | 12/2000 | Scherl |
| 6,187,021 | B1 | 2/2001 | Wim |
| 6,258,064 | B1 | 7/2001 | Smith et al. |
| 6,264,664 | B1 | 7/2001 | Avellanet |
| 6,406,484 | B1 | 6/2002 | Lang |
| 6,417,179 | B1 | 7/2002 | Burkhart et al. |
| 7,332,463 | B2 | 2/2008 | Greenberg |
| 7,500,981 | B1 | 3/2009 | Jubrail |
| 7,658,745 | B2 | 2/2010 | Olson |
| 7,875,267 | B2 | 1/2011 | Okajima et al. |
| 8,062,216 | B2 | 11/2011 | Raghuprasad |
| 2003/0187469 | A1 | 10/2003 | Olson |
| 2004/0126436 | A1 | 7/2004 | Cagle et al. |
| 2006/0085018 | A1 | 4/2006 | Clevenger |
| 2006/0156501 | A1 | 7/2006 | Grunberger |
| 2006/0253087 | A1 | 11/2006 | Vlodaver et al. |
| 2006/0287656 | A1 | 12/2006 | Brown et al. |
| 2007/0009368 | A1 | 1/2007 | Yang |
| 2008/0142385 | A1 | 6/2008 | Stein et al. |
| 2008/0234602 | A1 | 9/2008 | Oostman et al. |
| 2008/0300527 | A1* | 12/2008 | Bivins ............... A61F 13/38 604/1 |
| 2010/0017100 | A1 | 1/2010 | Yamamoto et al. |
| 2010/0082051 | A1 | 4/2010 | Thorpe et al. |
| 2010/0121363 | A1 | 5/2010 | Huttner et al. |
| 2010/0137814 | A1 | 6/2010 | Chew |
| 2010/0312198 | A1 | 12/2010 | Guidi |
| 2011/0015489 | A1 | 1/2011 | Raghuprasad |
| 2011/0017792 | A1 | 1/2011 | Stull et al. |
| 2011/0066172 | A1 | 3/2011 | Silverstein |
| 2011/0166421 | A1 | 7/2011 | Katiraei |
| 2012/0296355 | A1 | 11/2012 | Burres |
| 2013/0034103 | A1 | 2/2013 | Chen et al. |
| 2013/0304103 | A1 | 11/2013 | Burres |
| 2016/0302973 | A1 | 10/2016 | Kraitzer et al. |
| 2016/0302974 | A1 | 11/2016 | Chenal |

FOREIGN PATENT DOCUMENTS

| | | |
|---|---|---|
| CN | 2805725 Y | 8/2006 |
| CN | 201185988 Y | 1/2009 |
| CN | 201350157 Y | 11/2009 |
| CN | 101632612 A | 1/2010 |
| CN | 201426803 Y | 3/2010 |
| CN | 201481653 U | 5/2010 |
| CN | 201654722 U | 11/2010 |
| CN | 201719442 U | 1/2011 |
| CN | 201759743 U | 3/2011 |
| CN | 201894700 U | 7/2011 |
| CN | 202589763 U | 12/2012 |
| CN | 103006377 A | 4/2013 |
| DE | 20202497 U1 | 6/2002 |
| EP | 2412394 A1 | 2/2012 |
| FR | 2916135 A1 | 11/2008 |
| GB | 2520047 | 5/2015 |
| JP | S5410375 U | 1/1979 |
| JP | 2011036605 A | 2/2011 |
| JP | 2011115346 A | 6/2011 |
| JP | 2011229610 A | 11/2011 |
| JP | 2012030028 A | 2/2012 |
| JP | 3179742 U | 11/2012 |
| KR | 20100052442 A | 5/2010 |
| KR | 20110017792 A | 2/2011 |
| KR | 20120066413 A | 6/2012 |
| WO | 2009063978 | 5/2009 |
| WO | 2010017100 A1 | 2/2010 |
| WO | 2011085155 A2 | 7/2011 |
| WO | 2012023409 A1 | 2/2012 |
| WO | 2012158382 A1 | 11/2012 |
| WO | WO-2015083161 A1 * | 6/2015 ............ A61F 11/006 |

OTHER PUBLICATIONS

International Search Report PCT/IB2018/051965 Completed Jun. 22, 2018; dated Jul. 16, 2018 2 pages.

Written Opinion of the International Searching Authority PCT/IB2018/051965 dated Jul. 16, 2018 4 pages.

* cited by examiner

APPARATUS AND METHOD FOR TREATING OR/AND REFRESHING AN EAR CANAL

RELATED APPLICATIONS

This application is a National Phase of PCT Patent Application No. PCT/IB2018/051965 having International filing date of Mar. 23, 2018, which claims the benefit of priority of U.S. Provisional Application No. 62/475,920 filed on Mar. 24, 2017. The contents of the above applications are all incorporated by reference as if fully set forth herein in their entirety.

FIELD OF THE INVENTION

The present invention, in some embodiments thereof, relates to medical or hygienic techniques (apparatuses and methods) for treating or/and refreshing an ear canal of a subject, and more particularly, but not exclusively, to an apparatus, and a method, for treating or/and refreshing an ear canal, focused on cleaning the ear canal via removing cerumen therefrom.

BACKGROUND OF THE INVENTION

Ear wax blocking an ear canal, also known as cerumen impaction, is the number one reason of treatable hearing loss. It is also associated with serious sequelae, such as ear drum perforation, dizziness, ringing in the ear (tinnitus), social withdrawal, and poor work function. This phenomenon is very common and affects 5% of healthy adults, 10% of children, and up to 57% of elderly nursing home patients. Furthermore, hearing aids pitfall lies at their low efficiency when 60%-80% of hearing aids filters are blocked by earwax.

Current home use solutions for ear cleaning and hygiene are ineffective and might be harmful. The use of cotton swabs in ears is restricted by the FDA due to safety issues, main complication being tympanic membrane perforation. In certain cases, patients that don't clean their ears routinely may suffer from cerumen impaction, at this stage they would have to refer to a physician.

U.S. patent application Ser. No. 14/408,000 teaches about a cerumen removal apparatus for mechanically removing cerumen from an ear canal. The disclosed device comprises: a device body having a distal end and a proximal end interconnected by a main longitudinal axis; the distal end comprising at least one collector head for amassing the cerumen; the proximal end comprising at least one rotating mechanism adapted to rotate the at least one collector head; wherein the rotation of the collector head amasses the cerumen and removes the cerumen from the ear canal.

U.S. patent application Ser. No. 15/100,824 teaches about a device for removing earwax from an ear canal. The disclosed device includes a shaft; and an earwax collector head at an end of the shaft. The collector head is in the form of a helically shaped coil strip surrounding a substantially elongated space. The helically shaped coil strip has a cross section such that an outward facing surface thereof is substantially flat, and an interior surface thereof radially tapers to an inward facing edge. A distal end of the helically shaped coil strip tapers to present a wedge.

Although effective cerumen removal can be accomplished using helically shaped collector heads, such as those described above, use thereof in ears of some subjects, or/and by overly dynamic fashions, may cause inconvenience and pain to the subjects. Therefore, there is still a need for further inventions and modifications for increasing safety, efficacy or/and tolerability of apparatuses for treating or/and refreshing an ear canal.

SUMMARY OF THE INVENTION

The present invention, in some embodiments thereof, relates to medical or hygienic techniques (apparatuses and methods) for treating or/and refreshing an ear canal of a subject, and more particularly, but not exclusively, to an apparatus, and a method, for treating or/and refreshing an ear canal, focused on cleaning the ear canal via removing cerumen therefrom. In exemplary embodiments, the disclosed apparatus includes a treating element in the form of an elastic helically shaped coil strip, whose outer surface and inner surface may by coated (covered) by different possible combinations of outer layer, inner layer, and lubrication layer, coatings (coverings). In exemplary embodiments, the treating element outer surface and inner surface, as well as each of the outer layer, the inner layer, and the lubrication layer, are formed of, or/and include, materials that exhibit specific physicochemical properties and characteristics (particularly relating to friction and lubrication phenomena), which improve efficacy, safety, or/and tolerability of using the apparatus. In exemplary embodiments, the disclosed apparatus is used in a method for treating or/and refreshing an ear canal of a subject.

According to an aspect of some embodiments of the present invention, there is provided an apparatus for treating or/and refreshing an ear canal of a subject, the apparatus comprising: a treating element configured to radially outwardly press against wall of the ear canal when the apparatus is introduced into the ear canal, and to slide on the wall when rotated in the ear canal, thereby facilitating the treating or/and the refreshing of the ear canal, the treating element includes: a coil in a form of an elastic thin strip helically shaped around a central longitudinal axis of the treating element, the coil has a tubular coil outer surface and a tubular coil inner surface provided radially inwardly towards the coil outer surface relative to the central longitudinal axis; and an outer layer covering the coil outer surface; wherein, when the treating element is in a relaxed minimally-stressed configuration, the coil is configured with a first resisting pressure to radial compression of the coil outer surface relative to the central longitudinal axis, being smaller than a second resisting pressure to radial compression of the outer layer relative to the coil outer surface, thereby facilitating an increase in a total contact area with the wall when the outer layer radially compresses before the coil radially compresses, when the treating element radially outwardly presses against the wall.

According to some embodiments of the invention, the first resisting pressure to radial compression is within a range of 1.5 MPa to 10 MPa. According to some embodiments of the invention, the second resisting pressure to radial compression is within a range of 0.05 MPa to 1 MPa. According to some embodiments of the invention, a ratio of the first resisting pressure to the second resisting pressure is at least 10:1.

According to some embodiments of the invention, the outer layer has a thickness within a range of 0.1 mm to 0.5 mm. According to some embodiments of the invention, the outer layer includes a low-cushioning portion having a thickness within a range of 0.1 mm to 0.2 mm, or/and a high cushioning portion having a thickness within a range of 0.2 mm to 0.3 mm According to some embodiments of the invention, the thin strip is made of a first elastic material, and the outer layer is made of a second elastic material, wherein the second elastic material has a smaller Young modulus relative to Young modulus of the first elastic material. According to some embodiments of the invention, the second elastic material has a hardness within a range of 0 to 70 Shore A. According to some embodiments of the invention, the second elastic material is a silicon elastomer having a hardness of 20 to 30 Shore A. According to some embodiments of the invention, the first elastic material has a hardness of 70 Shore A to 70 Shore D. According to some embodiments of the invention, the first elastic material has a Young modulus equal to or greater than 100 MPa, and the second elastic material has a Young modulus equal to or less than 10 MPa. According to some embodiments of the invention, the second elastic material has a coefficient of friction equal to or greater than 0.8, and the first elastic material has a coefficient of friction equal to or less than 0.5.

According to some embodiments of the invention, the apparatus further comprises an inner layer of a third elastic material covering the coil inner surface, wherein the third elastic material has a greater coefficient of friction relative to the first elastic material. According to some embodiments of the invention, the third elastic material has a coefficient of friction equal to or greater than 0.6, and the first elastic material has a coefficient of friction equal to or less than 0.5.

According to some embodiments of the invention, the first elastic material is selected from the group consisting of: polyethylene (high density polyethylene), polypropylene, polyethylene terephthalate (PET), acrylonitrile butadiene styrene (ABS), Polyether ether ketone (PEEK), polyoxymethylene (acetal), nylon, metal, polycarbonate, and combinations thereof.

According to some embodiments of the invention, the second elastic material is selected from the group consisting of: polyurethane, thermoplastic polyurethane, silicone rubber, and combinations thereof.

According to some embodiments of the invention, the apparatus further comprises a lubrication layer that coats a portion or entirety of the outer layer or/and the coil outer surface, and comprises a lubricous material having surface characteristics configured to facilitate lubricated sliding when the treating element revolves against the wall. According to some embodiments of the invention, the lubricious material is selected from the group consisting of: hydrogel, polyvinylpyrrolidone (PVP), poly(acrylic acid) (PAA), hyaluronic acid, silicon oil, vegetable oil, and combinations thereof.

According to some embodiments of the invention, the apparatus further comprises an elongated body, from which the treating element protrudes, the elongated body is sized sufficiently to extend into the ear canal such that the treating element contacts the wall.

According to some embodiments of the invention, the treating element is configured to collect cerumen, and to hold the cerumen at the coil inner surface, when slidably rotating against the wall.

According to some embodiments of the invention, the coil includes a helical protrusion projecting inwardly from the coil inner surface towards the central longitudinal axis, the helical protrusion is configured to penetrate into the cerumen, or/and to transfer portion of the cerumen into contact with the coil inner surface, when the treating element rotates in the ear canal around or/and through the cerumen in a predetermined rotation direction.

According to an aspect of some embodiments of the present invention, there is provided an apparatus for treating or/and refreshing an ear canal of a subject, the apparatus comprising: a treating element configured to radially outwardly press against wall of the ear canal when the apparatus is introduced into the ear canal, and to slide on the wall when rotated in the ear canal, thereby facilitating the treating or/and the refreshing of the ear canal, the treating element includes: a coil in a form of an elastic thin strip made of a first material helically shaped around a central longitudinal axis of the treating element, the coil has a tubular coil outer surface and a tubular coil inner surface provided radially inwardly towards the coil outer surface relative to the central longitudinal axis; and an outer layer made of a second material covering the coil outer surface; wherein the second material has hardness within a range of 20 to 30 Shore A and a coefficient of friction equal to or greater than 0.8, such that the outer layer resists rotating motion of the treating element, or/and scrubs substances from surface of the wall, while radially outwardly pressing against the wall.

According to some embodiments of the invention, the outer layer prevents or minimizes irritation or pain to the subject when rotating against the wall with rotation velocities smaller than 10 RPM, optionally smaller than 7.5 RPM.

According to some embodiments of the invention, when the treating element is in a relaxed minimally-stressed configuration, the coil is configured with a first resisting pressure that resists radial compression of the coil outer surface relative to the coil central longitudinal axis, being less than a second resisting pressure that resists radial compression of the outer layer relative to the coil outer surface, thereby facilitating an increase in a total contact area with the wall when the outer layer radially compresses before the coil radially compresses, when the treating element radially outwardly presses against the wall.

According to some embodiments of the invention, the first resisting pressure resists radial compression in a range of 1.5 MPa to 10 MPa. According to some embodiments of the invention, the second resisting pressure resists radial compression in a range of 0.05 MPa to 1 MPa.

According to an aspect of some embodiments of the present invention, there is provided an apparatus for treating or/and refreshing an ear canal of a subject, the apparatus comprising: a treating element configured to radially outwardly press against wall of the ear canal when the apparatus is introduced into the ear canal, and to slide on the wall when rotated in the ear canal, thereby facilitating the treating or/and the refreshing of the ear canal, the treating element includes: a coil in a form of an elastic thin strip made of a first material helically shaped around a central longitudinal axis of the treating element, the coil has a tubular coil outer surface and a tubular coil inner surface provided radially inwardly towards the coil outer surface relative to the central longitudinal axis; and an outer layer made of a second material covering the coil outer surface; wherein, when the treating element is in a relaxed minimally-stressed configuration, the coil is configured with a first resisting pressure that resists radial compression of the coil outer surface relative to the coil central longitudinal axis, being less than a second resisting pressure that resists radial compression of the outer layer relative to the coil outer surface, thereby facilitating an increase in number of contact area portions distributed along and around the coil with the wall, when the treating element radially outwardly presses against the wall, thereby increasing spatial conformity of the treating element to a shape imposed by the wall.

According to an aspect of some embodiments of the present invention, there is provided a method for treating or/and refreshing an ear canal of a subject, the method comprising: providing an apparatus for treating or/and refreshing an ear canal of a subject, the apparatus comprises a treating element including: (1) a coil in a form of an elastic thin strip helically shaped in a chosen winding direction around a central longitudinal axis of the treating element, the coil has a tubular coil outer surface and a tubular coil inner surface provided radially inwardly towards the coil outer surface relative to the central longitudinal axis; and (2) an outer layer covering the coil outer surface; wherein, when the treating element is in a relaxed minimally-stressed configuration, the coil is configured with a first resisting pressure that resists radial compression of the coil outer surface relative to the central longitudinal axis, being smaller than a second resisting pressure that resists radial compression of the outer layer relative to the coil outer surface; introducing the treating element into the ear canal, such that a plurality of portions of the outer layer are compressed by way of pressing against a wall of the ear canal, thereby increasing total contact area of the treating element with the ear canal wall; rotating the treating element in the winding direction, so as to increase a diameter of the coil adjacent to each one of the compressed portions of the outer layer, thereby increasing conformity of shape of the treating element to a shape imposed by the ear canal wall; and distally advancing the treating element in the ear canal or/and repeating the rotating, thereby scrubbing and removing cerumen from the ear canal wall with the outer layer and directing the cerumen into contact with the coil inner surface.

According to such embodiments of the method, the first resisting pressure is within a range of 1.5 MPa to 10 MPa, and the second resisting pressure is within a range of 0.05 MPa to 1 MPa. According to such embodiments of the method, the rotating is performed using a rotation velocity less than 10 RPM. According to such embodiments of the method, the thin strip is made of a first material, and the outer layer is made of a second material, wherein the second material has a hardness within a range of 20 to 30 Shore A, and a coefficient of friction equal to or greater than 0.8, such that the outer layer resists rotating motion of the treating element while the treating element radially outwardly presses against the ear canal wall during the rotation.

All technical or/and scientific words, terms, or/and phrases, used herein have the same or similar meaning as commonly understood by one of ordinary skill in the art to which the invention pertains, unless otherwise specifically defined or stated herein. Exemplary embodiments of methods (steps, procedures), apparatuses (devices, systems, components thereof), equipment, and materials, illustratively described herein are exemplary and illustrative only and are not intended to be necessarily limiting. Although methods, apparatuses, equipment, and materials, equivalent or similar to those described herein can be used in practicing or/and testing embodiments of the invention, exemplary methods, apparatuses, equipment, and materials, are illustratively described below. In case of conflict, the patent specification, including definitions, will control.

BRIEF DESCRIPTION OF THE SEVERAL VIEW OF THE DRAWINGS

Some embodiments of the present invention are herein described, by way of example only, with reference to the accompanying drawings. With specific reference now to the drawings in detail, it is stressed that the particulars shown are by way of example and for purposes of illustrative description of some embodiments of the present invention. In this regard, the description taken together with the accompanying drawings make apparent to those skilled in the art how some embodiments of the present invention may be practiced.

In the drawings.

DESCRIPTION OF SPECIFIC EMBODIMENTS OF THE INVENTION

The present invention, in some embodiments thereof, relates to medical or hygienic techniques (apparatuses and methods) for treating or/and refreshing an ear canal of a subject, and more particularly, but not exclusively, to an apparatus, and a method, for treating or/and refreshing an ear canal, focused on cleaning the ear canal via removing cerumen therefrom. In exemplary embodiments, the disclosed apparatus includes a treating element in the form of an elastic helically shaped coil strip, whose outer surface and inner surface may by coated (covered) by different possible combinations of outer layer, inner layer, and lubrication layer, coatings (coverings). In exemplary embodiments, the treating element outer surface and inner surface, as well as each of the outer layer, the inner layer, and the lubrication layer, are formed of, or/and include, materials that exhibit specific physicochemical properties and characteristics (particularly relating to friction and lubrication phenomena), which improve efficacy, safety, or/and tolerability of using the apparatus. In exemplary embodiments, the disclosed apparatus is used in a method for treating or/and refreshing an ear canal of a subject.

According to an aspect of some embodiments of the present invention, there is provided an apparatus for treating or/and refreshing an ear canal of a subject. According to another aspect of some embodiments of the present invention, there is provided a method for treating or/and refreshing an ear canal of a subject, for example, involving use of the herein disclosed apparatus for treating or/and refreshing an ear canal of a subject.

The apparatus is maneuverable, optionally manually, to thereby generate the treating or/and the refreshing of the ear canal. The apparatus includes a treating element, which is sized and configured to press against wall portion of the ear canal and to slide thereon, when the apparatus is maneuverable and thereby optionally effecting rotation of the treating element inside the ear canal.

In some embodiments, the treating element includes a first portion having a tubular outer surface and a second portion having a tubular inner surface. The tubular inner surface is provided radially inwardly, and inwardly facing, towards the outer surface, relative to the central longitudinal axis of the treating element.

In some embodiments, the treating element is configured with the tubular outer surface for contacting the ear canal wall portion. Optionally and additionally, the treating element is configured with the tubular inner surface thereof to facilitate the treating or/and the refreshing of the ear canal when the treating element presses against, and slides on, the ear canal wall portion along a chosen sliding route. In some embodiments, the treating element is configured to collect cerumen, and to hold the cerumen at the tubular inner surface thereof, when slidably rotating against the ear canal wall portion. As such, the apparatus is particularly configured for removing cerumen from an ear canal of a subject.

In some embodiments, the tubular outer surface has surface physicochemical properties and characteristics providing a first coefficient of friction between the tubular outer surface and wall portion of the ear canal, and the tubular inner surface has surface physicochemical properties and characteristics providing a second coefficient of friction between the tubular inner surface and the ear canal wall portion or between the tubular inner surface and the cerumen. Optionally, the first coefficient of friction is less than the second coefficient of friction. Optionally, the surface physicochemical properties and characteristics of the tubular outer surface are dissimilar from the surface physicochemical properties and characteristics of the tubular inner surface.

In some embodiments, the treating element includes a helically shaped coil strip (i.e., a coil in a form of an elastic thin strip helically shaped around a central longitudinal axis of the treating element). The helically shaped coil strip has a tubular coil outer surface, and a tubular coil inner surface provided radially inwardly, and inwardly facing, towards the coil outer surface relative to the central longitudinal axis of the treating element. In some embodiments, the coil outer surface is partially or entirely coated (covered) with an outer layer coating (covering) having specific physicochemical properties and characteristics which improve safety, efficacy, or/and tolerability of the treating element during radially outwardly pressing against the ear canal wall, when the apparatus is introduced into the ear canal and revolves thereinside.

In some embodiments, when the treating element is in a relaxed minimally-stressed configuration, the coil is configured with a first resisting pressure that resists radial compression of the coil outer surface relative to the coil central longitudinal axis, optionally, within a range of 1.5 MPa to 10 MPa. In such relaxed configuration, additionally, the outer layer is configured with a second resisting pressure that resists radial compression relative to the coil outer surface, and which is substantially less than the first resisting pressure, optionally, within a range of 0.05 MPa to 1 MPa.

As such, the outer layer first compresses and deforms (e.g., flattens) at portions pressing against the ear canal wall before transferring therethrough necessary force to radially compress the coil. As a result, the negative counterpart of this radially compressing force, directing towards the ear canal wall, will be distributed throughout a greater contact area of the ear canal, and therefore, will affect a proportionally smaller pressure thereto.

Use of the treating element for removing cerumen is targeted mostly to the bony part of the ear canal, which has increased tendency to trauma and pain due to its smaller diameter and thinner skin layer. Unlike the outer cartilaginous region, having an 0.5 mm to 1 mm thick skin layer, the skin layer covering the osseous in the bony region is approximately 0.2 mm thick. The thinness of the skin and its adherence directly to the perichondrium or periosteum makes it particularly susceptible to bleeding when touched due to the lack of flexibility usually afforded by a subcutaneous layer of fat.

In some embodiments, the outer layer coating (covering) has a thickness within a range of 0.1 mm to 0.5 mm, so as to provide sufficient cushioning to the thin skin layer of the ear canal bony part. The outer layer may include a low-cushioning portion having a thickness within a range of 0.1 mm to 0.2 mm, or/and a high cushioning portion having a thickness within a range of 0.2 mm to 0.3 mm or more.

Implementation of the herein disclosed apparatus, and treating element thereof, provides another possible advantageous result of a more homogeneous radial compression of the coil when the coil is subjected to compressive forces from the ear canal wall, since more, or even substantially all, surface area of the era canal wall surrounding the coil is in contact (through the outer layer) with the outer surface of the radially compressing coil. Under more homogenous radial compression, the coil will better preserve its ability to collect and hold cerumen with its inner surface.

In some embodiments, the treating element coil outer layer coating (covering) is formed of a material provided in an elastic configuration, thereby effecting increased resistance during compression thereof, and having ability to regain nominal thickness when stress thereupon is relieved. Optionally and alternatively, the outer layer is formed of a material provided in a plastic configuration, thereby functioning as a mechanical damper when compressed.

In some embodiments, the elastic thin strip of the coil is made of a first material, and the outer layer coating (covering) is made of a second material configured with hardness within a range of 20 to 30 Shore A, and with a coefficient of friction equal to or greater than 0.8, such that the outer layer effectively resists rotating motion of the treating element, or/and scrubs substances from the surface of the ear canal wall while radially outwardly pressing against the ear canal wall surface. In exemplary embodiments, the outer layer is particularly configured to prevent or diminish irritation or pain to the subject when the treating element coil rotates against the ear canal wall with rotation velocities smaller than 10 rounds per minute (RPM), optionally, smaller than 7.5 rounds per minute (RPM).

The elastic thin strip of the coil is optionally made of a first elastic material, and the outer layer is made of a second elastic material having a Young modulus whose magnitude is less than that of the Young modulus of the first elastic material. The first elastic material optionally has a Young modulus equal to or greater than 100 MPa, while the second elastic material has a Young modulus equal to or less than 10 MPa. Optionally, additionally or alternatively, the first elastic material is configured with hardness of 70 Shore A to 70 Shore D, and the second elastic material is configured with hardness within a range of 0 to 70 Shore A. Optionally, the second elastic material is a silicon elastomer configured with hardness of 20 to 30 Shore A. Optionally, additionally or alternatively, the second elastic material forming the outer layer has a coefficient of friction equal to or greater than 0.8, optionally about 1, and the first elastic material forming the helically shaped coil strip has a coefficient of friction equal to or less than 0.5.

In some embodiments, the coil inner surface is coated (covered) with an inner layer coating (covering) made of a third elastic material. Optionally, the third elastic material forming the inner layer coating (covering) has a larger coefficient of friction relative to the first elastic material forming the coil, for example a coefficient of friction equal to or larger than 0.6, optionally equal to or larger than 0.8.

In some embodiments, the first elastic material is selected from the group consisting of: metal, polyethylene (high density polyethylene), polypropylene, polyethylene terephthalate (PET), acrylonitrile butadiene styrene (ABS), Polyether ether ketone (PEEK), polyoxymethylene (acetal), nylon, polycarbonate, and combinations thereof. In some embodiments, the second elastic material is selected from the group consisting of: polyurethane, thermoplastic polyurethane, silicone rubber, and combinations thereof.

In some embodiments, a portion or the entirety of the coil outer surface, or/and, a portion or the entirety of the outer layer coating (covering), is coated (covered) with a lubrication layer coating (covering). In exemplary embodiments, the lubrication layer coating (covering) is made of, or includes, a lubricous material having surface physicochemical properties and characteristics that facilitate lubricated sliding. Such lubricated sliding occurs via generation of lubrication or/and kinetic (dynamic) friction between the coil outer surface (or/and the outer layer) and the ear canal wall portion, when the treating element contacts and slidably revolves along the ear canal wall. In exemplary embodiments, the lubricious material is selected from the group consisting of: hydrogel, polyvinylpyrrolidone (PVP), poly (acrylic acid) (PAA), hyaluronic acid, silicon oil, vegetable oil, and combinations thereof.

The apparatus for treating or/and refreshing the ear canal may further include an elongated body, from which the treating element protrudes. The elongated body is sized sufficiently to extend into the ear canal, such that the treating element can contact the ear canal wall during the process of treating/refreshing (e.g., cerumen collecting, holding, and removing). The treating element is optionally configured to collect cerumen, and to hold the cerumen at, and along, the coil inner surface, when slidably rotating against the ear canal wall. The coil strip has a cross section having substantially flat or curved outer surface forming the coil outer surface, and a protrusion projecting inwardly from the coil inner surface towards the treating element central longitudinal axis. Optionally, the coil strip cross section is shaped as a wedge. The protrusion is helical along the length of the coil and is configured to penetrate into the cerumen, thread over it, or/and to transfer a portion of cerumen into contact with the coil inner surface, when the treating element rotates in the ear canal around or/and through the cerumen in a predetermined rotation direction (e.g., in the direction of the coil helices).

In exemplary embodiments, the treating element optionally includes a helix (helical, helically shaped or configured) type structure, so that the tubular outer surface thereof includes a helically curved portion revolving around the central longitudinal axis of the treating element. In some embodiments, the helix structure is flexible or/and subject to elastic (i.e., non-plastic) deformation in use, when the treating element is rotated inside the ear canal under normal forces applied by the user.

In exemplary embodiments, the treating element is configured, such that during implementation, when the helix structure is rotated in a same direction as the helically curved portion, relative to the central longitudinal axis (e.g., clockwise or counterclockwise), the treating element flexible helix structure 'opens up' or deform into a radially expanded shape and size, along length thereof, in a way that increases spatial conformity of the treating element to the ear canal shape imposed by its wall, therefore may result in increased treatment efficiency. Such possible 'opening up' or 'deforming' may happen, for example, when a friction force generated between a wall portion of the ear canal and the helically curved portion of the treating element tubular outer surface, which acts against the torque applied by the user to rotate the treating element, is sufficient to deform the flexible helix structure. In some such embodiments, the distribution or/and characteristics of outer layer about the coil outer surface increases the overall contact area with the ear canal wall, increases the overall friction force applied to the coil, or/and increases number of dispersed contact/clinging portions, by way of compaction or flattening at contact portions with different portions of the ear canal wall, or/and by way of higher coefficient of friction thereof relative to surface characteristics of the coil itself.

For purposes of further understanding exemplary embodiments of the present invention, in the following illustrative description thereof, reference is made to the figures (FIGS. 1 through 4). Throughout the following description and accompanying drawings, same reference numbers refer to same components, elements, or features. It is to be understood that the invention is not necessarily limited in its application or to particular details of construction or/and arrangement of exemplary device, apparatus, or/and system components, set forth in the following illustrative description. The invention is capable of other exemplary embodiments or of being practiced or carried out in various ways.

Figure 1:
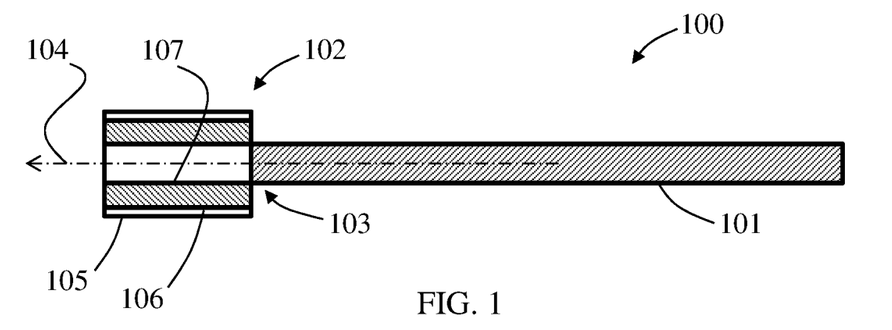
FIG. 1 schematically illustrates a side cross sectional view of an exemplary apparatus for treating or/and refreshing an ear canal of a subject, according to some embodiments of the invention.
Figure 2A:
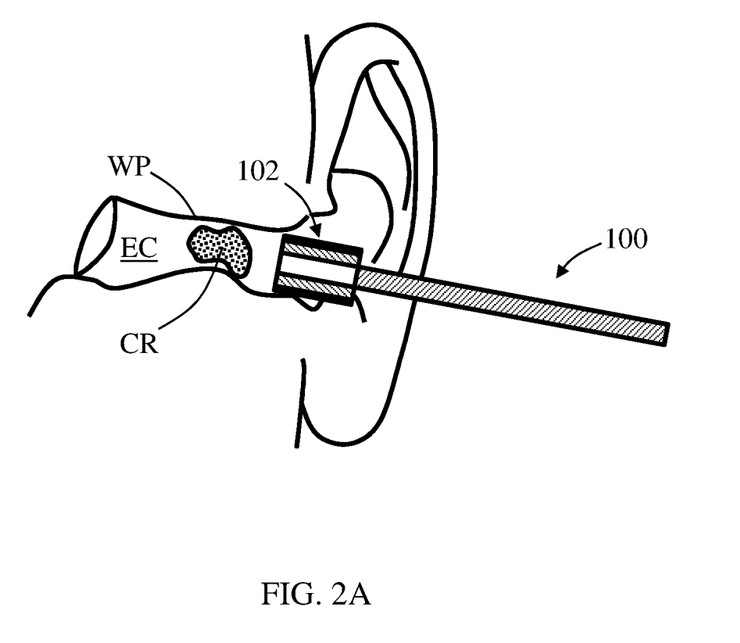
FIGS. 2A-2C schematically illustrate different scenarios representing possible exemplary steps in a method for treating or/and refreshing an ear canal using the apparatus shown in FIG. 1, according to some embodiments of the invention.
Figure 2B:
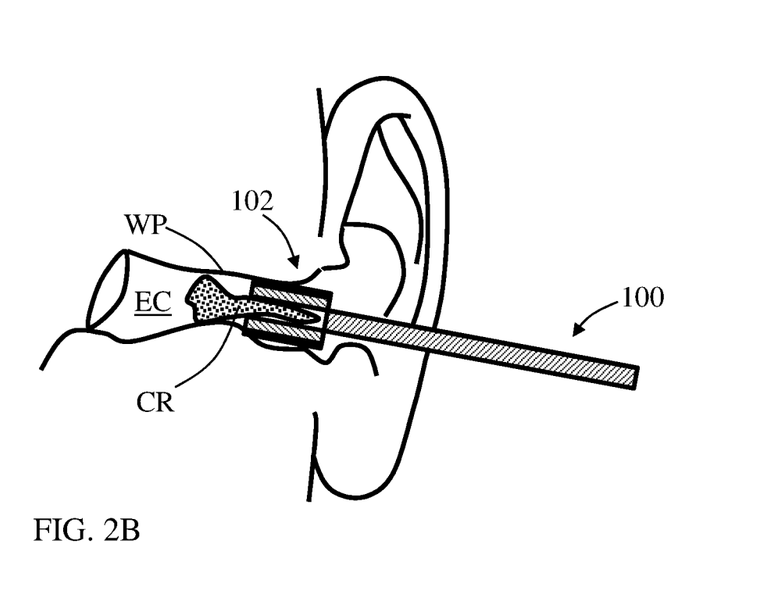
Figure 2C:
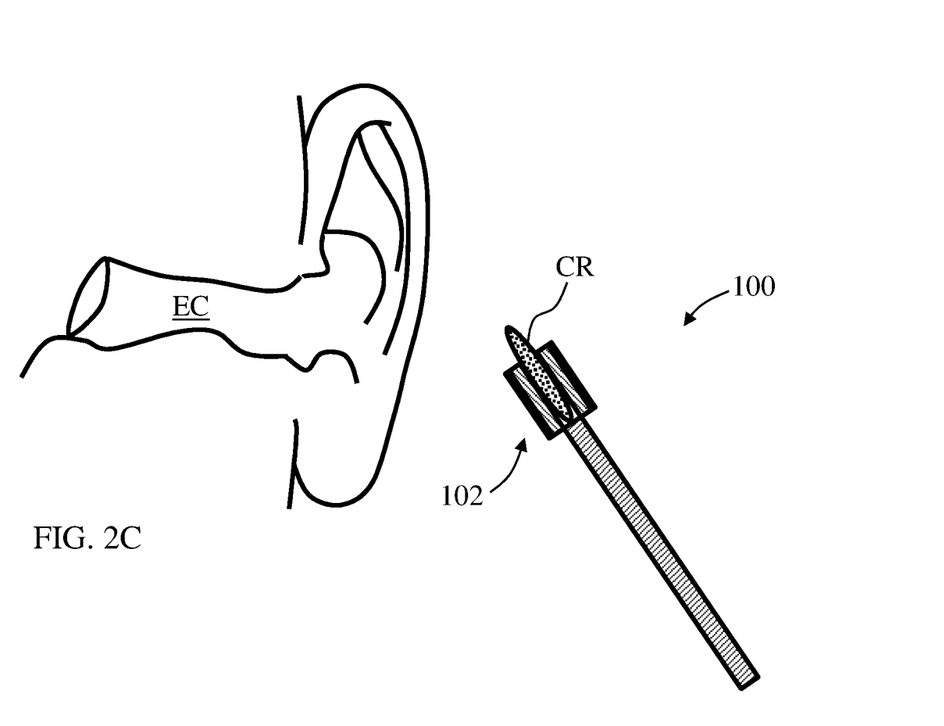

FIG. 1 schematically illustrates a side cross sectional view of an exemplary apparatus 100 for treating or/and refreshing an ear canal of a subject. FIGS. 2A-2C schematically illustrate different scenarios representing possible exemplary steps in a method for treating or/and refreshing an ear canal EC of a subject, involving using apparatus 100 for cleaning the ear canal via removing cerumen CR therefrom.

Apparatus 100 includes an elongated body 101 and a treating element 102 protruding radially-outwardly from distal end 103 of elongated body 101 relative to the central longitudinal axis 104 of treating element 102. In exemplary embodiments, elongated body 101 and treating element 102 are designed and constructed as an integrally (monolithically) formed, single structure. In alternative exemplary embodiments, elongated body 101 is designed and constructed as a first (stand-alone) structure, and treating element 102 is designed and constructed as a second separate (stand-alone) structure, whereby both structures are operatively connectable to each other, such that apparatus 100 will be in the form of an overall single structure.

Treating element 102 is sized and configured to contact, press against, and slide along, a wall portion WP of the ear canal EC, when apparatus 100 is maneuverable (e.g., rotates around or/and travels along central longitudinal axis 104), to effect the treating or/and the refreshing of the ear canal EC. Elongated body 101 has sufficient length to extend into the ear canal EC, such that treating element 102 contacts and continuously presses against wall portion WP of the ear canal.

Treating element 102 and elongated body 101 each have elasticity and rigidity properties and characteristics that are sufficient for facilitating treating or/and refreshing differently shaped ear canals of different subjects. Chosen elastic characteristics allow conformity to different shapes, curvatures, or/and size dimensions (e.g., diameters, lengths) of the ear canals, when a moderate degree of force is radially applied to surrounding wall (e.g., ear canal wall portion WP) of the ear canal. Chosen rigidity of treating element 102 is required for providing sufficient resistance to deformations when treating element 102 is pressed against the ear canal wall and slides thereon. Treating element 102 is made of, or includes, a polymeric material selected from the group consisting of: polyethylene, polypropylene, polyethylene terephthalate (PET), acrylonitrile butadiene styrene (ABS), Polyether ether ketone (PEEK), polyoxymethylene (acetal), nylon, metal, polycarbonate, and combinations thereof.

In exemplary embodiments, treating element 102 includes a tubular outer surface 106, and a tubular inner surface 107.

In exemplary embodiments, tubular outer surface 106 is coated (covered) by an outer layer coating (covering), for example, outer layer 105. Outer layer 105 is formed of an elastic material having smaller resistance to radial compression than materials forming the rest of treating element 102. In exemplary embodiments, elastic material of outer layer 105 has a radial compression within a range of 0.05 MPa to 1 MPa, relative to the materials of the remainder of treating element 102 having radial compression within a range of 1.5 MPa to 10 MPa, or more.

In exemplary embodiments, tubular inner surface 107 is configured radially inwardly, and inwardly facing, towards tubular outer surface 106, relative to central longitudinal axis 104. In exemplary embodiments, tubular inner surface 107 facilitates treating or/and refreshing of ear canal EC when treating element 102 contacts, presses against, and slides on ear canal wall portion WP along a chosen sliding route. As particularly shown in FIGS. 2B-2C, treating element 102 is configured to collect cerumen CR, and to partially or completely hold cerumen CR at tubular inner surface 107, when tubular inner surface 107 slidably rotates against ear canal wall portion WP.

In exemplary embodiments, outer layer 105 is configured so as to reduce hardness of the rest of treating element 102 from about 65 Shore D down to about 60 Shore A, when outer layer 105 is coated with polyurethane, or down to about 20 Shore A, when outer layer 105 is coated with silicone rubber, for example.

In some embodiments, outer layer 105 includes several layers of coating applied onto tubular outer surface 106. Optionally, each coating layer includes one or more different coating materials or compositions. In some such embodiments, layers of different coating materials are so chosen and configured, such that Shore hardness and coefficient of friction are minimized (in order to diminish or prevent discomfort and potential harm to the ear canal and to other tissues, for example). In some embodiments, a first or an intermediate coating layer serves as an agent for facilitating or enhancing bonding or adhesion of another coating layer. In exemplary embodiments, outer layer 105 is composed of a first coating layer overlaying tubular outer surface 106, which includes silicone rubber, polyurethane or thermoplastic polyurethane, and a second coating layer, overlaying the first coating layer, which includes hydrogel; the first coating layer may provide required resistance to radial compression, and/or other characteristics such as elasticity and hardness, while the second coating layer exhibits an appropriate coefficient of friction. Optionally the first layer or another intermediate layer and is configured to enhance adhesion between the first coating layer and the second coating layer.

Figure 3A:
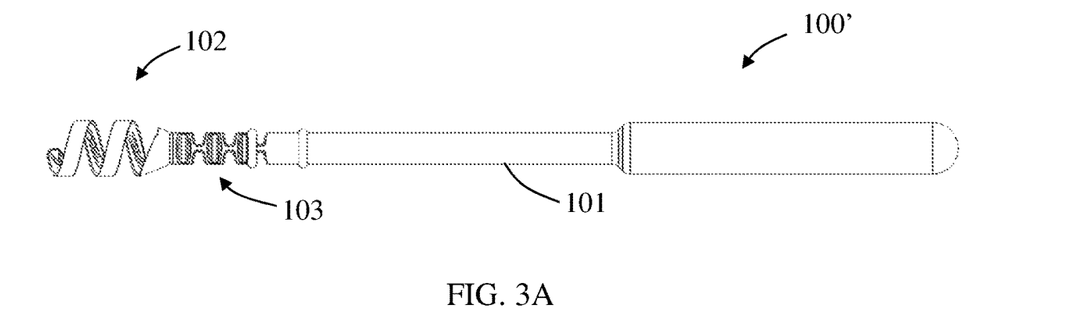
FIG. 3A schematically illustrates a side view of an exemplary apparatus for treating or/and refreshing an ear canal of a subject, according to some embodiments of the invention.
Figure 3B:
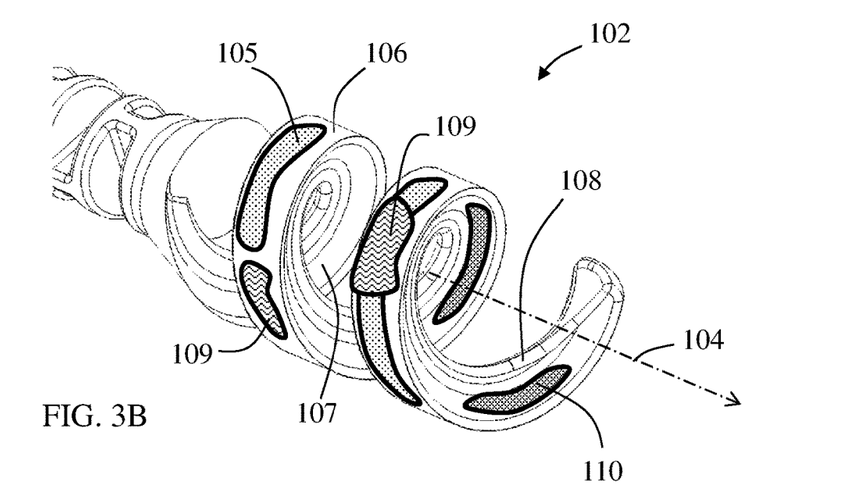
FIG. 3B schematically illustrates a perspective view of the exemplary apparatus shown in FIG. 3A, highlighting outer layer, inner layer, and lubrication layer, coatings (coverings) of the apparatus treating element, according to some embodiments of the invention.

FIGS. 3A-3B schematically illustrate a side view and a perspective view, respectively, of apparatus 100', which is an exemplary particular configuration of apparatus 100, for treating or/and refreshing, via removing cerumen from, an ear canal of a subject. FIG. 3B particularly highlights different exemplary embodiments of outer layer, inner layer, and lubrication layer, coatings (coverings) of the apparatus treating element.

In this particular exemplary configuration of apparatus 100', treating element 102 is in a form of a coil strip helically shaped around central longitudinal axis 104. In exemplary embodiments, treating element 102 (herein, also referred to as coil 102), in the form of a helically shaped coil strip, has a tubular coil outer surface 106, and a tubular coil inner surface 107 provided radially inwardly, and inwardly facing, towards coil outer surface 106 relative to central longitudinal axis 104. Optionally, tubular outer surface 106 has an N2 type surface finish (i.e., a lapping surface finish) to an N4 type surface finish (i.e., a grinding surface finish), and tubular inner surface 107 has an N5 type surface finish (i.e., a grinding surface finish) to an N8 type surface finish (i.e., a smooth machining surface finish).

In exemplary embodiments, coil outer surface 106 is partially or entirely covered (coated) with an outer layer 105 coating (covering), as described hereinabove for apparatus 100 shown in FIG. 1. For example, as particularly shown in FIG. 3B, coil outer surface 106 is only partially covered (coated) with outer layer 105. In alternative exemplary embodiments, coil outer surface 106 can be entirety covered (coated) with outer layer 105.

In exemplary embodiments, coil inner surface 107 is partially or entirely covered (coated) with an inner layer 110 coating (covering). For example, as particularly shown in FIG. 3B, coil inner surface 107 is only partially covered (coated) with inner layer 110. In alternative exemplary embodiments, coil inner surface 107 can be entirety covered (coated) with inner layer 110. In exemplary embodiments, inner layer 110 coating (covering) is formed of a material having a greater coefficient of friction relative to the material forming treating element coil 102, optionally at least 0.6, optionally at least 0.8, optionally about 1.

In exemplary embodiments, the coil strip has a width within a range of about 1 mm to about 3 mm (optionally, about 1.5 mm), and a thickness (calculated as shortest distance between coil outer surface and coil inner surface) within a range of 0.1 mm to 1 mm, optionally about 0.5 mm. The coil strip spans around tubular boundaries having a length within a range of about 5 mm to about 20 mm, optionally about 10 mm, and outer diameter within a range of about 2 mm to about 7.5 mm (for example, about 4.2 mm, about 5.4 mm, or about 6.5 mm). The coil pitch (the distance in between adjacent coil loops) is within a range of 1 mm to 10 mm, optionally about 4 mm.

Treating element 102 further includes a helical protrusion 108 projecting inwardly from tubular inner surface 107 towards central longitudinal axis 104. Height of helical protrusion 108, measured from tubular inner surface 107 towards central longitudinal axis 104, is optionally in a range of about 0.1 mm to 1 mm, optionally about 1 mm. Helical protrusion 108 is configured to penetrate into cerumen CR, or/and to transfer a portion of cerumen CR into contact with coil inner surface 107, when treating element 102 rotates in ear canal EC around or/and through cerumen CR in a predetermined rotation direction (clockwise or counterclockwise, in accordance with the helical route of protrusion 108 around central longitudinal axis 104, for example).

In exemplary embodiments, coil outer layer 105 is partially or entirely coated (covered) with a lubrication layer 109 coating (covering). Additionally, or alternatively, coil outer surface 106 is partially or entirely coated (covered) with lubrication layer 109 coating (covering). For example, as shown in FIG. 3B, each of coil outer layer 105, and coil outer surface 106, is partially coated with lubrication layer 109, where most of lubrication layer 109 resides on coil outer layer 105, while some of lubrication layer 109 resides on coil outer surface 106. In exemplary embodiments, lubrication layer 109 has surface characteristics that facilitate generation of lubricated and kinetic friction between tubular outer surface 106 and ear canal wall portion WP, when treating element 102 slidably rotates along and presses against ear canal wall portion WP.

In exemplary embodiments, lubricating layer 109 coating (covering) is, or includes, a form of lubricious material, that is fixatable to tubular outer surface 106 by way of chemical etching, plasma coating or thermal spraying, for example. The lubricious material may include one or any combination of hydrogel, polyvinylpyrrolidone (PVP), poly(acrylic acid) (PAA), hyaluronic acid, silicon oil, polyurethane, and vegetable oil.

Figure 4:
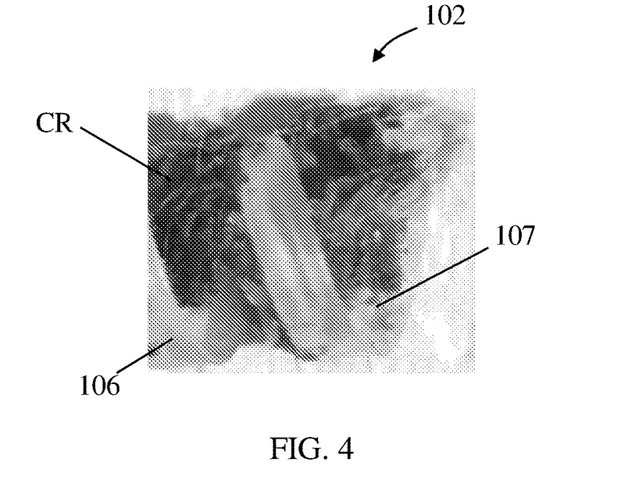
FIG. 4 is an exemplary image showing cerumen collected and held in a treating element of an apparatus similar to the apparatus shown in FIGS. 3A-3B, according to some embodiments of the invention.

FIG. 4 is an exemplary image showing cerumen CR collected and held in a treating element 102 of an apparatus similar to apparatus 100' shown in FIGS. 3A-3B. As shown in FIG. 4, cerumen CR collected by treating element 102 is in direct contact with, and held by, coil inner surface 107.

According to another aspect of some embodiments of the present invention, there is provided a method for treating or/and refreshing an ear canal of a subject, for example, involving use of the herein disclosed apparatus for treating or/and refreshing an ear canal of a subject. In exemplary embodiments, such a method includes the following steps (procedures).

Providing an apparatus for treating or/and refreshing an ear canal of a subject. For implementing the method, the provided apparatus for treating or/and refreshing the ear canal of the subject may be any of the hereinabove illustratively described exemplary embodiments of such apparatus, for example, apparatus 100 (shown in FIGS. 1, 2A-2C), or apparatus 100' (shown in FIGS. 3A-3B).

In exemplary embodiments, for implementing the method, such an apparatus has a treating element that includes the following components and functions thereof.

First, a coil in a form of an elastic thin strip helically shaped in a chosen winding direction around a central longitudinal axis of the treating element, whereby the coil has a tubular coil outer surface and a tubular coil inner surface provided radially inwardly towards the coil outer surface relative to the central longitudinal axis.

Second, an outer layer covering the coil outer surface, wherein, when the treating element is in a relaxed minimally-stressed configuration, the coil is configured with a first resisting pressure that resists radial compression of the coil outer surface relative to the central longitudinal axis, being smaller than a second resisting pressure that resists radial compression of the outer layer relative to the coil outer surface.

Introducing the treating element into the ear canal, such that a plurality of portions of the outer layer are compressed by way of pressing against a wall of the ear canal, thereby increasing total contact area of the treating element with the ear canal wall.

Rotating the treating element in the winding direction, so as to increase a diameter of the coil adjacent to each one of the compressed portions of the outer layer, thereby increasing conformity of the shape of the treating element to a shape imposed by the ear canal wall.

Distally advancing the treating element in the ear canal or/and repeating the rotating, thereby scrubbing and removing cerumen from the ear canal wall with the outer layer and directing the cerumen into contact with the coil inner surface.

In exemplary embodiments of the method, in the coil of the provided apparatus, the first resisting pressure is within a range of 1.5 MPa to 10 MPa, and the second resisting pressure is within a range of 0.05 MPa to 1 MPa. In additional exemplary embodiments of the method, the step (procedure) of rotating is performed using a rotation velocity less than 10 RPM.

In additional exemplary embodiments of the method, in the provided apparatus, elastic thin strip is made of a first material, and the coil outer layer is made of a second material. In such embodiments, for example, the second material has a hardness within a range of 20 to 30 Shore A, and a coefficient of friction equal to or greater than 0.8, such that the outer layer resists rotating motion of the treating element while the treating element radially outwardly presses against the ear canal wall during the rotation.

In additional exemplary embodiments, the method may further include additional steps (procedures), and sub-steps (sub-procedures) thereof, for example, as illustratively described hereinabove, along with reference to FIGS. 1, 2A-2C, 3A-3B, and 4.

Each of the following terms written in singular grammatical form: 'a', 'an', and 'the', as used herein, means 'at least one', or 'one or more'. Use of the phrase 'one or more' herein does not alter this intended meaning of 'a', 'an', or 'the'. Accordingly, the terms 'a', 'an', and 'the', as used herein, may also refer to, and encompass, a plurality of the stated entity or object, unless otherwise specifically defined or stated herein, or, unless the context clearly dictates otherwise. For example, the phrases: 'a unit', 'a device', 'an assembly', 'a mechanism', 'a component', 'an element', and 'a step or procedure', as used herein, may also refer to, and encompass, a plurality of units, a plurality of devices, a plurality of assemblies, a plurality of mechanisms, a plurality of components, a plurality of elements, and, a plurality of steps or procedures, respectively.

Each of the following terms: 'includes', 'including', 'has', 'having', 'comprises', and 'comprising', and, their linguistic/grammatical variants, derivatives, or/and conjugates, as used herein, means 'including, but not limited to', and is to be taken as specifying the stated component(s), feature(s), characteristic(s), parameter(s), integer(s), or step(s), and does not preclude addition of one or more additional component(s), feature(s), characteristic(s), parameter(s), integer(s), step(s), or groups thereof. Each of these terms is considered equivalent in meaning to the phrase 'consisting essentially of'.

The term 'method', as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed invention.

Throughout this disclosure, a numerical value of a parameter, feature, characteristic, object, or dimension, may be stated or described in terms of a numerical range format. Such a numerical range format, as used herein, illustrates implementation of some exemplary embodiments of the invention, and does not inflexibly limit the scope of the exemplary embodiments of the invention. Accordingly, a stated or described numerical range also refers to, and encompasses, all possible sub-ranges and individual numerical values (where a numerical value may be expressed as a whole, integral, or fractional number) within that stated or described numerical range. For example, a stated or described numerical range 'from 1 to 6' also refers to, and encompasses, all possible sub-ranges, such as 'from 1 to 3', 'from 1 to 4', 'from 1 to 5', 'from 2 to 4', 'from 2 to 6', 'from 3 to 6', etc., and individual numerical values, such as '1', '1.3', '2', '2.8', '3', '3.5', '4', '4.6', '5', '5.2', and '6', within the stated or described numerical range of 'from 1 to 6'. This applies regardless of the numerical breadth, extent, or size, of the stated or described numerical range.

Moreover, for stating or describing a numerical range, the phrase 'in a range of between about a first numerical value and about a second numerical value', is considered equivalent to, and meaning the same as, the phrase 'in a range of from about a first numerical value to about a second numerical value', and, thus, the two equivalently meaning phrases may be used interchangeably. For example, for stating or describing the numerical range of room temperature, the phrase 'room temperature refers to a temperature in a range of between about 20° C. and about 25° C.', and is considered equivalent to, and meaning the same as, the phrase 'room temperature refers to a temperature in a range of from about 20° C. to about 25° C.'.

The term 'about', as used herein, refers to ±10% of the stated numerical value.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub-combination in the context or format of a single embodiment, may also be illustratively described and presented in the context or format of a plurality of separate embodiments.

Although the invention has been illustratively described and presented by way of specific exemplary embodiments, and examples thereof, it is evident that many alternatives, modifications, or/and variations, thereof, will be apparent to those skilled in the art. Accordingly, it is intended that all such alternatives, modifications, or/and variations, fall within the spirit of, and are encompassed by, the broad scope of the appended claims.

All publications, patents, and or/and patent applications, cited or referred to in this disclosure are herein incorporated in their entirety by reference into the specification, to the same extent as if each individual publication, patent, or/and patent application, was specifically and individually indicated to be incorporated herein by reference. In addition, citation or identification of any reference in this specification shall not be construed or understood as an admission that such reference represents or corresponds to prior art of the present invention. To the extent that section headings are used, they should not be construed as necessarily limiting.

What is claimed is:

1. An apparatus for treating or/and refreshing an ear canal of a subject, the apparatus comprising:
   a treating element configured to radially outwardly press against wall of the ear canal when the apparatus is introduced into the ear canal, and to slide on said wall when rotated in the ear canal, thereby facilitating the treating or/and the refreshing of the ear canal,
   said treating element includes:
   a coil in a form of an elastic thin strip helically shaped around a central longitudinal axis of said treating element, said coil has a tubular coil outer surface and a tubular coil inner surface provided radially inwardly towards said coil outer surface relative to said central longitudinal axis; and
   an outer layer covering said coil outer surface;
   wherein, said coil is configured with a first resisting pressure to radial compression of said coil outer surface relative to said central longitudinal axis, being greater than a second resisting pressure to radial compression of said outer layer relative to said coil outer surface, thereby facilitating an increase in a total contact area with said wall when said outer layer radially compresses before said coil radially compresses, when said treating element radially outwardly presses against said wall.

2. The apparatus according to claim 1, wherein said first resisting pressure to radial compression is within a range of 1.5 MPa to 10 MPa, and/or wherein said second resisting pressure to radial compression is within a range of 0.05 MPa to 1 MPa, and/or
   wherein a ratio of said first resisting pressure to said second resisting pressure is at least 10:1.

3. The apparatus according to claim 1, wherein said outer layer has a thickness within a range of 0.1 mm to 0.5 mm.

4. The apparatus according to claim 1, wherein said outer layer includes a low-cushioning portion having a thickness within a range of 0.1 mm to 0.2 mm, or/and a high cushioning portion having a thickness within a range of 0.2 mm to 0.3 mm.

5. The apparatus according to claim 1, wherein said thin strip is made of a first elastic material, and said outer layer is made of a second elastic material, wherein said second elastic material has a smaller Young modulus relative to a Young modulus of said first elastic material.

6. The apparatus according to claim 5, wherein said first elastic material has a hardness of 70 Shore A to 70 Shore D, and/or wherein said second elastic material has a hardness within a range of 0 to below 70 Shore A.

7. The apparatus according to claim 5, wherein said first elastic material has a Young modulus equal to or greater than 100 MPa, and said second elastic material has a Young modulus equal to or less than 10 MPa.

8. The apparatus according to claim 5, wherein said second elastic material has a coefficient of friction equal to or greater than 0.8, and said first elastic material has a coefficient of friction equal to or less than 0.5.

9. The apparatus according to claim 5, further comprising an inner layer of a third elastic material covering said coil inner surface, wherein said third elastic material has a greater coefficient of friction relative to said first elastic material.

10. The apparatus according to claim 9, wherein said third elastic material has a coefficient of friction equal to or greater than 0.6, and said first elastic material has a coefficient of friction equal to or less than 0.5.

11. The apparatus according to claim 5, wherein said first elastic material is selected from the group consisting of: polyethylene (high density polyethylene), polypropylene, polyethylene terephthalate (PET), acrylonitrile butadiene styrene (ABS), Polyether ether ketone (PEEK), polyoxymethylene (acetal), nylon, metal, polycarbonate, and combinations thereof.

12. The apparatus according to claim 5, wherein said second elastic material is manufactured from a material selected from the group consisting of: a silicon elastomer having a hardness of 20 to 30 Shore A, polyurethane, thermoplastic polyurethane, silicone rubber, and combinations thereof.

13. The apparatus according to claim 1, further comprising a lubrication layer that coats a portion or entirety of said outer layer or/and said coil outer surface and comprises a lubricous material having surface characteristics configured to facilitate lubricated sliding when said treating element revolves against said wall.

14. The apparatus according to claim 13, wherein said lubricious material is selected from the group consisting of: hydrogel, polyvinylpyrrolidone (PVP), poly(acrylic acid) (PAA), hyaluronic acid, silicon oil, vegetable oil, and combinations thereof.

15. The apparatus according to claim 1, further comprising an elongated body, from which said treating element protrudes, said elongated body is sized sufficiently to extend into the ear canal such that said treating element contacts said wall and wherein said treating element is configured to collect cerumen, and to hold said cerumen at said coil inner surface, when slidably rotating against said wall, and wherein said coil includes a helical protrusion projecting inwardly from said coil inner surface towards said central longitudinal axis, said helical protrusion is configured to penetrate into said cerumen, or/and to transfer a portion of said cerumen into contact with said coil inner surface, when said treating element rotates in the ear canal around or/and through said cerumen in a predetermined rotation direction.

16. The apparatus according to claim 1, wherein said treating element is configured with an increase in the spatial conformity thereof to a shape imposed by said wall, when said treating element radially outwardly presses against said wall.

17. An apparatus for treating or/and refreshing an ear canal of a subject, the apparatus comprising:
a treating element configured to radially outwardly press against wall of the ear canal when the apparatus is introduced into the ear canal, and to slide on said wall when rotated in the ear canal, thereby facilitating the treating or/and the refreshing of the ear canal,
said treating element includes:
a coil in a form of an elastic thin strip made of a first material helically shaped around a central longitudinal axis of said treating element, said coil has a tubular coil outer surface and a tubular coil inner surface provided radially inwardly towards said coil outer surface relative to said central longitudinal axis; and
an outer layer made of a second material covering said coil outer surface;
wherein said second material has a hardness within a range of 20 to 30 Shore A and a coefficient of friction equal to or greater than 0.8, such that said outer layer resists rotating motion of said treating element, or/and scrubs substances from surface of said wall, while radially outwardly pressing against said wall.

18. The apparatus according to claim 17, wherein said outer layer is configured to prevent or minimize irritation or pain to the subject when rotating against said wall with rotation velocities smaller than 10 RPM.

19. A method for treating or/and refreshing an ear canal of a subject, the method comprising:
providing an apparatus for treating or/and refreshing an ear canal of a subject, said apparatus comprises a treating element including: (1) a coil in a form of an elastic thin strip helically shaped in a chosen winding direction around a central longitudinal axis of said treating element, said coil has a tubular coil outer surface and a tubular coil inner surface provided radially inwardly towards said coil outer surface relative to said central longitudinal axis; and (2) an outer layer covering said coil outer surface; wherein, said coil is configured with a first resisting pressure that resists radial compression of said coil outer surface relative to said central longitudinal axis, being greater than a second resisting pressure that resists radial compression of said outer layer relative to said coil outer surface;
introducing said treating element into the ear canal, such that a plurality of portions of said outer layer are compressed by way of pressing against a wall of the ear canal, thereby increasing total contact area of said treating element with said ear canal wall;
rotating said treating element in said winding direction, so as to increase a diameter of said coil adjacent to each one of said compressed portions of said outer layer, thereby increasing conformity of shape of said treating element to a shape imposed by said ear canal wall; and
distally advancing said treating element in the ear canal or/and repeating said rotating, thereby scrubbing and removing cerumen from said ear canal wall with said outer layer and directing said cerumen into contact with said coil inner surface.

20. The method according to claim 19, wherein said rotating is performed using a rotation velocity less than 10 RPM.

* * * * *